United States Patent [19]

Oxenrider, Bryce C. et al.

[11] 4,455,349

[45] Jun. 19, 1984

[54] MIXTURES COMPRISING HYDROCARBON ESTERS OF BENZENE CARBOXYLIC ACIDS AND FLUOROCARBON ESTERS OF BENZENE CARBOXYLIC ACIDS AND FIBERS CONTAINING THE SAME

[75] Inventors: Oxenrider, Bryce C., Florham Park; Alson K. Price, Chester, both of N.J.

[73] Assignee: Allied Corporation, Morris Township, Morris County, N.J.

[21] Appl. No.: 516,506

[22] Filed: Jul. 25, 1983

Related U.S. Application Data

[62] Division of Ser. No. 374,840, May 5, 1982, Pat. No. 4,410,717.

[51] Int. Cl.$^3$ ............... D02G 3/00; D06M 13/46; C08G 63/12
[52] U.S. Cl. ............... 428/395; 8/115.6; 252/8.6; 252/8.8; 428/364; 524/323
[58] Field of Search ............... 428/375, 394, 395, 364; 8/115.5, 115.6; 252/8.6, 8.8, 8.9; 524/323; 560/37, 87, 89; 528/191, 299, 302, 310, 401

[56] References Cited

U.S. PATENT DOCUMENTS

| | | | |
|---|---|---|---|
| 4,209,610 | 6/1980 | Mares et al. | 8/115.5 |
| 4,250,300 | 2/1981 | Saegusa et al. | 528/401 |
| 4,283,292 | 8/1981 | Marshall et al. | 8/115.6 |
| 4,290,765 | 9/1981 | Sandler | 8/115.6 |
| 4,321,403 | 3/1982 | Oxenrider et al. | 560/87 |

*Primary Examiner*—Lorraine T. Kendell
*Attorney, Agent, or Firm*—Alan M. Doernberg; Gerhard H. Fuchs; Kenneth E. Stroup

[57] ABSTRACT

Tetraesters of pyromellitic dianhydride are disclosed wherein two ester moieties are saturated hydrocarbon groups and two ester moieties are halohydroxyalkyl groups. The compounds may be used as diluents for fluorinated pyromellitates that are useful as soil and water repelling agents. Mixtures formed by dissolving the compounds of this invention and known fluorinated pyromellitates in a common solvent are capable of imparting soil and water repelling properties to various fibers that are essentially equivalent to soil and water repelling properties imparted to such fibers by fluorinated pyromellitates alone. Additionally, the hydrocarbon pyromellitates of this invention may be used alone as water repellents.

14 Claims, No Drawings

MIXTURES COMPRISING HYDROCARBON ESTERS OF BENZENE CARBOXYLIC ACIDS AND FLUOROCARBON ESTERS OF BENZENE CARBOXYLIC ACIDS AND FIBERS CONTAINING THE SAME

This application is a division of application Ser. No. 374,840, filed May 5, 1982, now U.S. Pat. No. 4,410,717.

BACKGROUND OF THE INVENTION

This invention relates to novel compounds and compositions derived and formed from polycarboxy benzene dianhydrides. More specifically, the invention relates to esters synthesized by reacting polycarboxy benzene dianhydrides with saturated alcohols and epoxide containing radicals, and to mixtures which are composed of the described hydrocarbon esters and partially fluorinated esters of polycarboxy benzene dianhydrides. Such compounds and compositions are useful as soil and water repelling agents.

The use of fluorinated pyromellitates as surface modifiers is disclosed in U.S. Pat. No. 4,209,610 (Mares et al., 1980). Mares et al. discloses pyromellitate tetraesters wherein two ester moieties are perfluorinated alkyl groups and two ester moieties are halohydroxyalkyl groups.

We have unexpectedly discovered that mixtures composed of hydrocarbon esters of polycarboxy benzene dianhydrides and fluorinated esters of polycarboxy benzene dianhydrides impart soil and oil repellancy to various fibers. The hydrocarbon esters are inexpensive in comparison to the fluorinated esters. Therefore, the discovery is advantageous in that soil and oil repelling compositions may be produced more economically than the corresponding soil and oil repelling fluorinated compounds derived from polycarboxy benzene dianhydrides.

BRIEF DESCRIPTION OF THE INVENTION

This application is a divisional application of application Ser. No. 374,840 filed May 5, 1982 and allowed on June 7, 1983.

The present invention relates to compounds having the structure

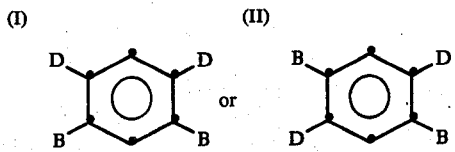

or mixtures thereof wherein B is $COOCHOHCH_2Q$ where Q is Cl, OH, H, or Br, and D is $COW(CH_2)_nCH_3$, with W being $-O-$, $-NH-$, $-S-$ or $-N(CH_3)-$, and n being an integer from 2 to 24. Additionally, this invention relates to novel mixtures comprising between about 20 and 50 weight percent of a first component represented by structure I or II (or mixtures thereof) as described above, and between about 50 and 80 weight percent of a second component represented by a compound having the structure

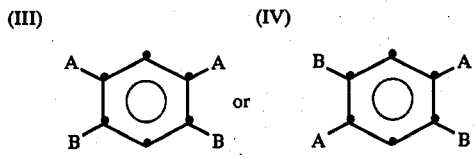

or mixtures thereof wherein A is $COWX(CF_2)_pCF_3$ with W being $-O-$, $-S-$, $-NH-$, or $-N(CH_3)-$; wherein X is alkylene of 1-6 carbons with p being an integer from 3 to 15, and B is the same as in structure I or II. In the preferred embodiments of this invention the novel mixtures are comprised of between about 30 and 35 percent of component I or II (or mixtures thereof) and between about 65 and 70 percent of component III or IV, or mixtures thereof.

Our invention also includes polyethylene terephthalate and nylon fibers, especially nylon 6 and nylon 66 fibers, having incorporated therewith the compositions as above defined.

DETAILED DESCRIPTION OF THE INVENTION

A major disadvantage is associated with the use of fluorinated pyromellitates as soil and water repellents. The disadvantage is that fluorinated soil and water repellents are very expensive to produce. The high cost of production of fluorinated soil and water repellents is directly related to the high cost of fluorinated alcohol starting materials. Therefore, the discovery of compounds that are inexpensive in comparison to the fluorinated compounds and which may be used as diluents for the fluorinated compounds would be advantageous. This would be true, of course, only if the mixtures formed by the addition of a diluent were found to impart soil and water repelling characteristics to fibers that parallel the soil and water repelling characteristics imparted to fibers treated with only fluorocarbon compounds.

We have surprisingly discovered that hydrocarbon esters of pyromellitic dianhydride when used in admixture with partially fluorinated esters of pyromellitic dianhydride disclosed in U.S. Pat. No. 4,209,610 (Mares et al., 1980) result in a mixture that imparts soil and oil repelling characteristics to fibers that parallel soil and oil repelling characteristics imparted to fibers containing only the compounds of U.S. Pat. No. 4,209,610. This finding was most unexpected as our own experimental work had demonstrated that the use of hydrocarbon esters of pyromellitic dianhydride by themselves did not impart soil and oil repelling characteristics to fibers. Furthermore, this discovery was additionally unexpected due to the fact our experimental work had also demonstrated that compounds prepared by reacting pyromellitic dianhydride with a mixture of fluorocarbon and hydrocarbon alcohols also did not impart equivalent soil and oil repelling characteristics to fibers.

The novel hydrocarbon compounds of the present invention are represented by the general structure

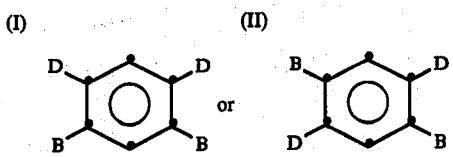

or mixtures thereof wherein B is COOCHOHCH$_2$Q where Q is Cl, OH, H, or Br and D is COW(CH$_2$)$_n$CH$_3$, with W being —O—, —NH—, —S— or —N(CH$_3$)—, and n is an integer from 2 to 24. In the preferred embodiments of this invention Q in the above formula is Cl, W is 0, and N is 1 to 6.

Another embodiment of this invention is the use of the above-described pyromellitates alone where n is 14 to 20 as water repelling agents. In the preferred embodiment of this aspect of the invention, n is 17. The longer chain hydrocarbon pyromellitates are extremely hydrophobic and are very desirable water repelling compounds. The use of these compounds as water repelling agents is illustrated in Example 4 of this application.

The above-described hydrocarbon esters may be synthesized in general by initially reacting an alkanol with pyromellitic dianhydride to form an intermediate diester-diacid. This intermediate is then reacted with an epoxide containing radical to synthesize the desired hydrocarbon ester compound. The procedure for synthesizing the compounds of this invention is essentially the same as that described in U.S. Pat. No. 4,209,610 for the compounds disclosed by that patent, except that instead of using fluorinated alcohols and fluorinated amines, the compounds of this invention require saturated hydrocarbon alcohols and saturated hydrocarbon amines.

In the preferred embodiments of this invention the novel hydrocarbon esters of pyromellitic dianhydride are combined with the partially fluorinated esters of pyromellitic dianhydride disclosed in U.S. Pat. No. 4,209,610 to form mixtures of the described esters.

The mixtures are formed by simply dissolving the esters in a common solvent to form a homogeneous solution. Suitable solvents for forming the solutions include chloroform, dioxane, acetone, and other similar solvents.

The fluorinated esters of pyromellitic dianhydride useful for the practice of this invention have the general structure

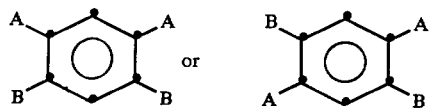

(III)     (IV)

or mixtures thereof wherein A is COWX(CF$_2$)$_p$CF$_3$ with W being —O—, —NH—, —S— or —N(CH$_3$)—; wherein X is alkylene of 1–6 carbons and p is from 3 to 15 with B being of the formula COOCH$_2$CHOHCH$_2$Q; wherein Q is Cl, OH, H, or Br.

The preferred fluorinated pyromellitates for the practice of this invention are those derived from fluorinated hydrocarbyl ethanols represented by the formula CF$_3$(CF$_2$)$_p$CH$_2$CH$_2$O— where p is a commercial mixture of 3–15, but is preferably 3–13. Slightly less preferred are those derived from fluorinated hydrocarbyl propanols and from fluorinated hydrocarbyl butanols. Substituents A with alkylenes of 1–6 carbons other than 1,2-ethylene, 1,2-propylene or 1–4-butylene may also be used, but are less preferred.

The novel mixtures of the present invention comprise between about 20 and 50 weight percent of the non-fluorinated ester of pyromellitic dianhydride, and between about 50 and 80 weight percent of the fluorinated ester of pyromellitic dianhydride. In the preferred embodiments of this invention the novel compositions contain between about 30 and 35 weight percent of the non-fluorinated ester of pyromellitic dianhydride and between about 65 and 70 weight percent of the fluorinated ester of pyromellitic dianhydride.

The mixtures of the present invention may be incorporated into nylon and polyethylene terephthalate fibrers according to the procedure described in U.S. Pat. No. 4,209,610. In general, incorporation of the compositions into such fibers is accomplished by contacting such fibers with a liquid emulsion, dispersion or solution which contains a composition as described above, and thereafter usually heating this fiber sufficiently to develop water and oil repellency thereof which is retained at least in substantial part after five standard dry cleaning cycles and after five standard home laundering cycles.

EXAMPLE 1

Into a dry one liter round bottom flask fitted with a thermometer, stirring bar, water cooled condenser, dropping funnel and a bleed of dry nitrogen to maintain an anhydrous atmosphere, was added pyromellitic dianhydride (81.3 g, 0.373 mol) and dry 1-methyl-2-pyrrolidone (75 mL). 1-Hexanol (76.2 g, 0.746 mol) was added over about 20 minutes and the exothermic reaction was not allowed to go above 54° C. The reaction mixture was then stirred under nitrogen at a constant temperature of 45° C. for 22 hours to insure complete reaction. Triethyl amine (3.1 mL) was added as catalyst, the temperature was raised to 55° C. and epichlorohydrin (175 mL, 2.24 mol) was added via a dropping funnel over 45 minutes. The reaction was monitored by following the disappearance of carboxyl groups by titration and was complete within 6.5 hours. The reaction mixture was cooled to room temperature and then poured into well agitated ice water (2500 mL) and stirred for 30 minutes to extract water soluble material. The washing procedure was repeated once with fresh ice water and the product was then taken up in a mixture of dichloromethane (200 mL) and dichloroethane (100 mL). The solution was filtered and flash evaporated with the product (210.4 g, 0.304 mol) being recovered as a very viscous red-brown liquid. The structure was confirmed by proton NMR.

EXAMPLE 2

The procedure was essentially the same as that described in Example 1. The pyromellitic dianhydride (32.7 g, 0.15 mol) in 1-methyl-2-pyrrolidone (25 mL) was reacted with ethanol (17.5 mL, 0.3 mol) and the intermediate diester-diacid was further reacted with epichlorohydrin (70.34 mL, 0.9 mol) and with triethylamine (1.25 mL) as catalyst at 55° C. The reaction was complete in six hours and the product (64.9 g) was recovered as before. The structure was confirmed by proton NMR.

EXAMPLE 3

Four solutions were prepared in acetone in order to determine the oil repellency of nylon-6 tricot fabric that was treated with one of the four solutions. The first solution contained 0.1% of the commercially available difluoroalkyl-dichlorohydrin tetraester of Example 1 as disclosed in U.S. Pat. No. 4,321,403 (Oxenider et al., 1982) hereinafter referred to as DSR. The second solution contained 0.15% DSR. The third solution contained 0.1% DSR and 0.05% of the product from Example 2 of this application hereinafter referred to as H2DSR. The fourth solution contained 0.1% DSR and 0.05% of the product from Example 1 of this application hereinafter referred to as H1DSR. Four nylon swatches were each dipped in only one of the solutions, air dried for one hour, and then annealed in a circulating air oven at 120° C. for 0.5 hours. The initial oil repellency was determined by the standard AATCC oil droplet test, and again after subsequent laundering in an automatic washing machine and drying in an electric dryer. The fabric swatches were not ironed after drying. The results appear in Table I. The oil repellency values in Table 1 correspond to the rating values utilized for oil repellency by the American Assocation of Textile Colorists and Chemists.

TABLE I

| Additive | Oil Repellencies No. of Cycles | | | | | | | |
|---|---|---|---|---|---|---|---|---|
| | 0 | 1 | 2 | 3 | 4 | 5 | 6 | 7 |
| .1% DSR | 7 | 7 | 7 | 6 | 5 | 2 | | |
| .15% DSR | 7 | 7 | 7 | 6 | 6 | 5 | 4 | 1 |
| .1% DSR + .05% H2DSR | 7 | 7 | 6 | 6 | 6 | 4 | 2 | |
| .1% DSR + .05% H1DSR | 7 | 6 | 6 | 5 | 4 | 4 | 4 | 4 |

EXAMPLE 4

To a dry 200 mL round bottom flask, N₂ atmosphere, was added pyromellitic dianhydride (10.9 g, 0.05 mol), 1-octadecanol (27.1 g, 0.1 mol) and DMF (27 mL). React at 45° C. for 22 hours. The reaction mixture had set up and was heated to 60° C. to liquify. Epicholorhydrin (23.5 mL, 0.29 mol) and triethylamine (0.42 mL) were added and within 5.25 hours the reaction was completed. The reaction mixture was cooled to room temperature and poured into rapidly-agitated ice water (1200 mL). The water was decanted and the precipitate was washed four additional times. The product was recovered by filtration and was dried under vacuum yielding 38.2 grams of a cream colored solid. The structure was confirmed by proton NMR.

0.5 % was coated on nylon 6 tricot fabric as previously described. There was no oil repellency by AATCC Test. However, the AATCC water spray test indicated a water repellency that was somewhat stable to home laundering. The results appear in Table II.

TABLE II

| Cycles | Spray Rating |
|---|---|
| 0 | 90 |
| 1 | 90 |
| 2 | 80 |
| 3 | 70 |
| 4 | 50 |
| 5 | 0 |

We claim:

1. A mixture comprising between about 20 and 50 weight percent of a first component consisting of a compound having the formula

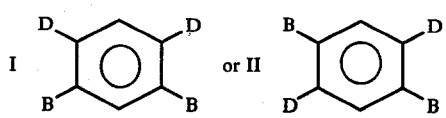

or mixtures thereof wherein B is

where Q is Cl, OH, H, or Br, and D is

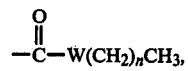

with W being —O—, —NH—, —S— or —N(CH₃)— and n being an integer from 2 to 24 and between about 50 and 80 weight percent of an additional component, consisting of a compound of the formula

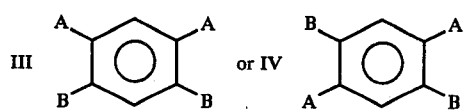

or mixtures thereof wherein A is

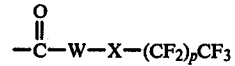

with W being —O—, —NH—, —S—, or —N(CH₃)—; wherein X is alkylene of 1-6 carbons and p is an integer from 3 to 15 with B being the same as in said first component.

2. A mixture in accordance with claim 1 wherein Q is Cl.

3. A mixture in accordance with claim 2 wherein W is O.

4. A mixture in accordance with claim 3 wherein n is 1-6.

5. A mixture according to claim 1 wherein X is —CH₂—CH₂— and p is 3-13.

6. A mixture according to claim 1 comprising between about 30 and 35 weight percent of said first component, and between about 65 and 70 weight percent of said additional component.

7. A nylon fiber having incorporated therewith the mixture of claim 1.

8. A polyethylene terephthalate fiber having incorporated therewith the mixture of claim 1.

9. A nylon fiber having incorporated therewith the mixture of claim 6.

10. A polyethylene terephthalate fiber having incorporated therewith the mixture of claim 6.

11. A nylon 6 fiber having incorporated therewith the mixture of claim 1.

12. A nylon 66 fiber having incorporated therewith the mixture of claim 1.

13. A nylon 6 fiber having incorporated therewith the mixture of claim 6.

14. A nylon 66 fiber having incorporated therewith the mixture of claim 6.

* * * * *